United States Patent [19]
Dombrowski et al.

[11] Patent Number: 4,978,344
[45] Date of Patent: Dec. 18, 1990

[54] NEEDLE AND CATHETER ASSEMBLY

[76] Inventors: Mitchell P. Dombrowski, 103 Mapleton, Grosse Point Farms, Mich. 48236; Robert A. Welch, 9573 Winterset Cir., Plymouth, Mich. 48170

[21] Appl. No.: 269,784

[22] Filed: Dec. 27, 1988

Related U.S. Application Data

[63] Continuation-in-part of Ser. No. 231,053, Aug. 11, 1988, abandoned.

[51] Int. Cl.$^5$ ............................................. A61M 5/32
[52] U.S. Cl. .................................... 604/198; 604/263
[58] Field of Search ............... 604/110, 111, 192, 197, 604/198, 199, 263, 171, 163

[56] References Cited

U.S. PATENT DOCUMENTS

| 4,564,054 | 1/1986 | Gustavsson | 604/198 |
| 4,652,256 | 3/1987 | Vaillancourt | 604/52 |
| 4,659,330 | 4/1987 | Nelson et al. | 604/192 |
| 4,725,267 | 2/1988 | Vaillancourt | 604/192 |
| 4,735,618 | 4/1988 | Hagen | 604/192 |
| 4,762,516 | 8/1988 | Luther et al. | 604/164 |
| 4,790,828 | 12/1988 | Dombrowski et al. | 604/198 |
| 4,795,432 | 1/1989 | Karczmer | 604/110 |
| 4,795,443 | 1/1989 | Permenter et al. | 604/198 |
| 4,832,696 | 5/1989 | Luther et al. | 604/164 |
| 4,846,809 | 7/1989 | Sims | 604/198 |

Primary Examiner—John D. Yasko
Assistant Examiner—Adam J. Cermak

[57] ABSTRACT

A disposable needle assembly (10) includes a hub (16) for connecting the assembly (10) to a fluid conduit, the hub (16) including a passageway (24) extending therethrough. A hollow needle portion (28) is in fluid communication with the passageway (24). A cap (34) has a neutral position along the needle portion (28) proximate to the hub (16) for exposing a length of the needle portion (28) and an extended position for capping the distal tip (32) of the needle (28). The cap (34) is reversibly seated in engagement with a catheter assembly as the needle portion (28) is disposed within a passageway of the catheter assembly whereby removal of the needle portion (28) from the passageway of the catheter assembly moves the cap (34) to the extended position capping the distal tip (32) as the cap (34) is unseated from the catheter assembly. The invention further provides a method of catherizing a patient using a disposable needle assembly (10).

22 Claims, 3 Drawing Sheets

U.S. Patent  Dec. 18, 1990  Sheet 1 of 3  4,978,344
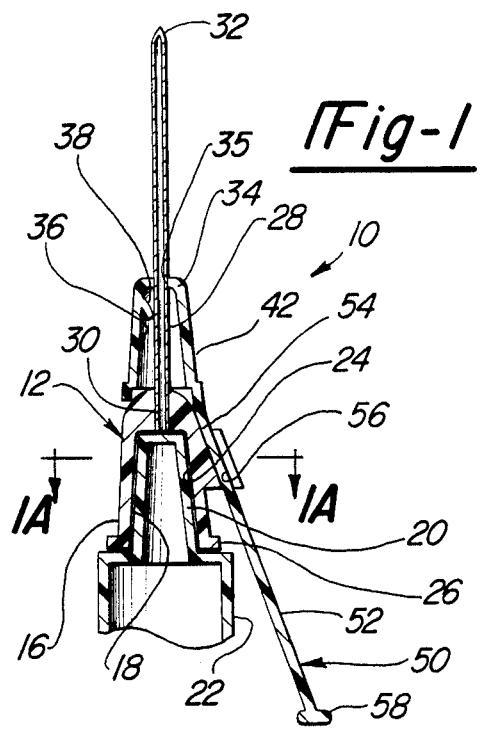
*Fig-1*
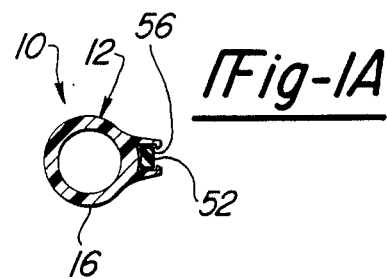
*Fig-1A*
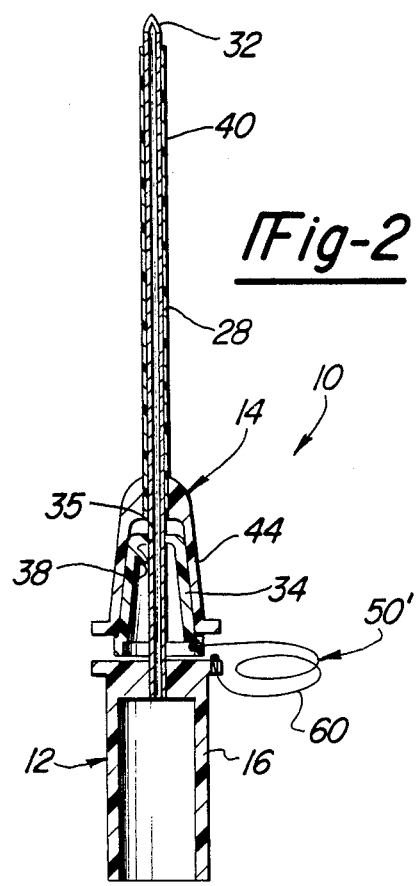
*Fig-2*
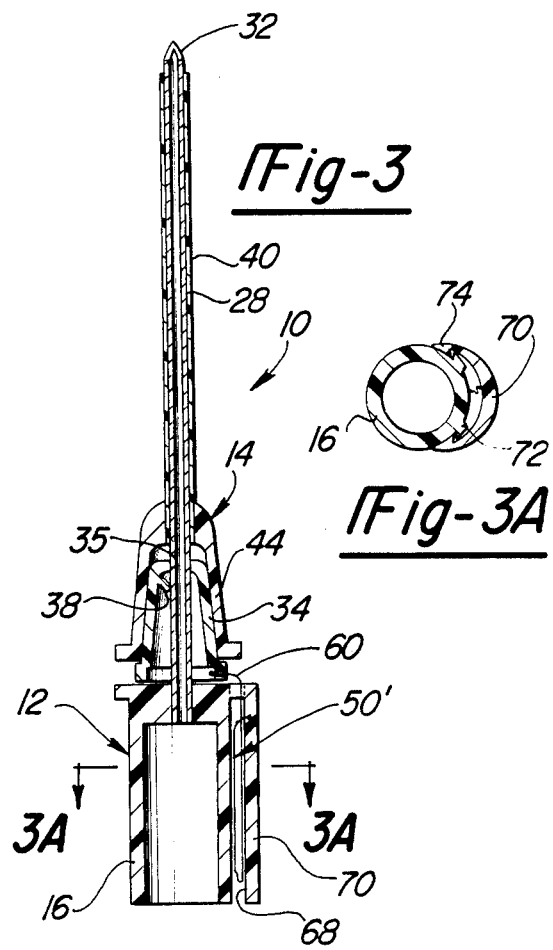
*Fig-3*
*Fig-3A*

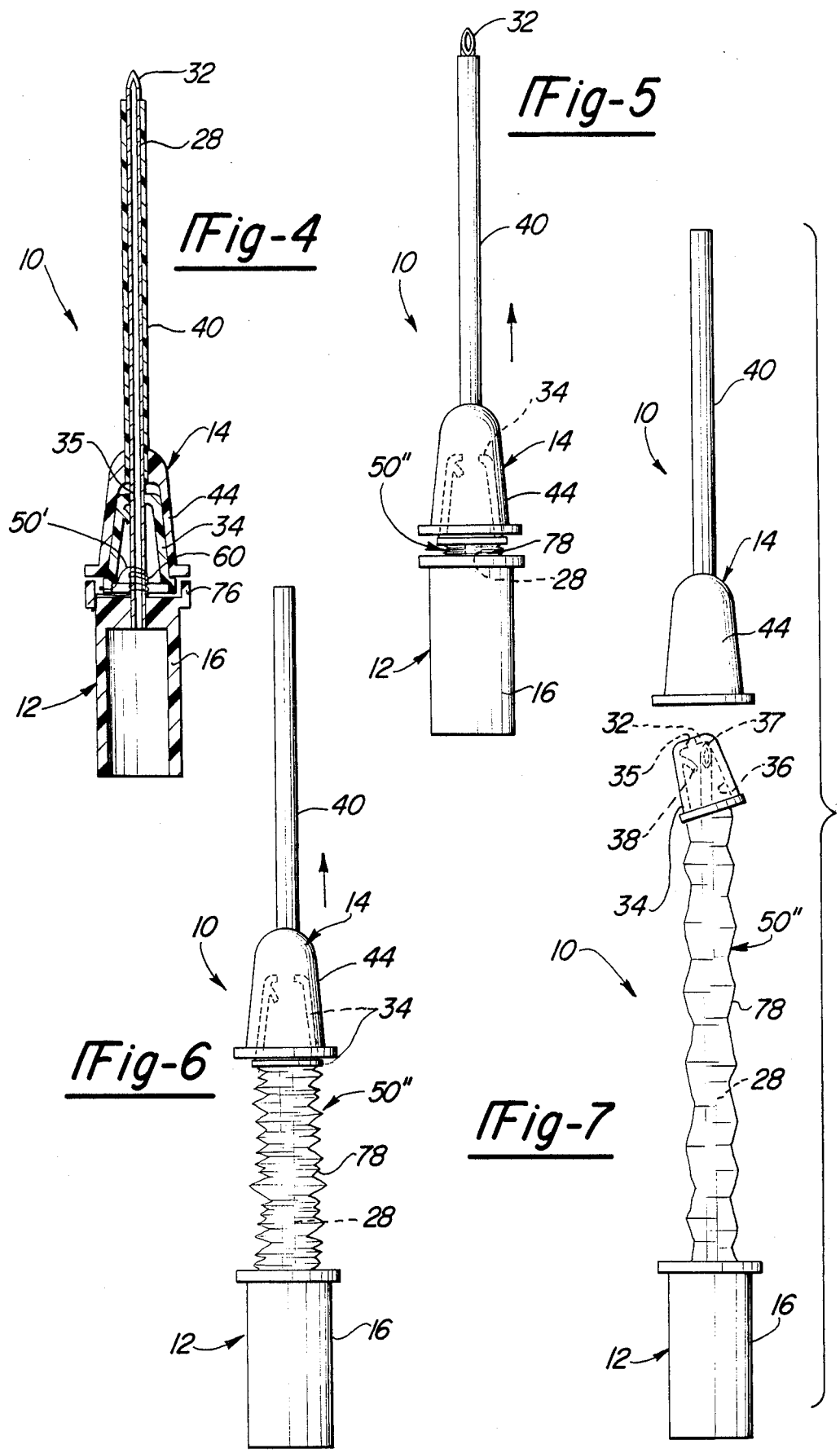

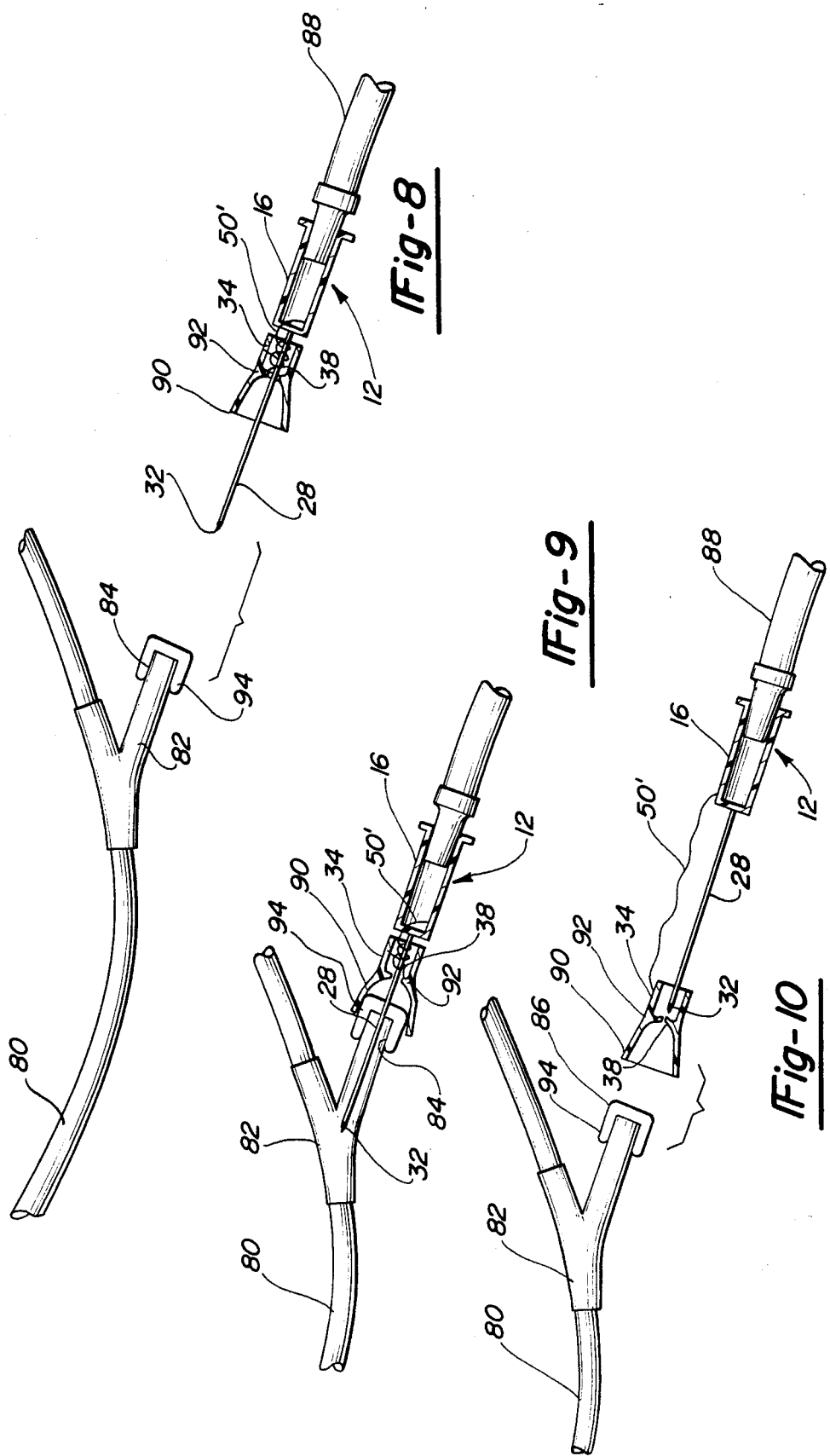

NEEDLE AND CATHETER ASSEMBLY

This application is a continuation-in-part of U.S. Ser. No. 231,053 filed Aug. 11, 1988, abandoned.

TECHNICAL FIELD

This invention relates generally to disposable needle assemblies for use in combination with a hypodermic syringe apparatus, and more specifically relates to a disposable needle assembly particularly well suited for use in combination with a catheter disposed over a needle to cap the distal end of the needle upon displacement of the needle from the catheter.

BACKGROUND ART

There exists a continued risk of exposure to infectious agents by health care workers who are continually utilizing hypodermic syringe assemblies for injecting patients with medicaments. Because of this situation, it has been recommended that all needles used by health care workers should be regarded as potentially infective and handled with extraordinary care to prevent accidental injuries. Health care workers are advised to place disposable needles in puncture resistant containers. However, it is practically impossible to place puncture resistant containers in every patient's room and every office of a medical facility.

The U.S. Pat. Nos. 3,134,380 to Armao, issued May 26, 1964; 3,658,061 to Hall, issued Apr. 25, 1972; and 4,139,009 to Alverez, issued Feb. 13, 1979, all relate to hypodermic needle assemblies which attempt to shield a used hypodermic needle after use. The Hall patent discloses a catheter needle guard unit including a hub with a needle affixed thereto and a needle guard including a sleeve member with a longitudinal slot adapted to snap over the entire length of the needle. In operation, the needle guard is in the open position when the needle is used to make a venipuncture in a patient and snapped into the closed position manually by a finger of the operator after withdrawal of the needle.

The Armao and Alverez patents both disclose retractable needle guards which extend over the length of the needle assembly prior to use and are retracted as the needle is inserted into the patient.

A device manufactured by ICU Medical, Inc. of Huntington Beach, California and marked "ICU High Risk" ® includes locking members mounted on the needle shaft and a shield which has a neutral position wherein the shield is disposed against the hub and an extended position wherein the shield is disposed over the tip.

The Armao, Alverez, and ICU Medical, Inc. assemblies all include a shield which covers a significant portion of the needle shaft during use of the needle for an injection. Hence, the assemblies either have less usable needle length if a conventional needle is adapted to the assembly or the assemblies require a significantly longer needle shaft. Additionally, all of these assemblies leave the tip of the needle exposed or capable of being exposed. The tip of the needle is not locked in a completely enclosed guard.

The U.S. Pat. No. 4,735,618 to Hagen, issued Apr. 5, 1988, discloses a protective enclosure for a hypodermic syringe having a needle guard connected to a hub portion by two pair of pivotally moveable arms which operate to permit the needle to pass through a central channel during injection and rest in a needle pocket when injection has been completed. Similar to the aforementioned devices, the Hagen patent provides a needle guard having an extended neutral position. The needle guard must be forced back along the needle shaft during injection.

The U.S. Pat. No. 4,790,828, issued Dec. 13, 1988 to the applicant of the present application, discloses a disposable needle assembly including a cap having a neutral unstressed position proximate to the hub of the needle exposing a length of the needle portion and an extended stressed position wherein the cap is biased towards the neutral position for irreversibly capping the distal tip of the needle. A tether connects the cap to the hub portion.

The present invention provides an improvement to the self-capping needle assembly disclosed in applicant's prior patent application by providing an assembly adapted to be used in combination with a catheter. Further, the present invention provides improved forms of tethers for connecting the cap to the hub portion of the needle.

SUMMARY OF THE INVENTION

In accordance with the present invention there is provided a disposable needle assembly including first hub means for connecting the assembly to a fluid conduit, the first hub means including a passageway extending therethrough and a hollow needle portion in fluid communication with the passageway. The hollow needle portion includes a distal tip. Cap means includes a neutral position along the needle portion proximate to the first hub means for exposing a length of the needle portion and an extended position for capping the distal tip. The cap means includes seating means for reversibly seating the cap means in engagement with a catheter assembly as the needle portion is disposed within a passageway of the catheter assembly whereby removal of the needle portion from the passageway of the catheter assembly moves cap means to the extended position capping the distal tip as the cap means is unseated from the catheter assembly.

FIGURES IN THE DRAWINGS

Other advantages of the present invention will be readily appreciated as the same becomes better understood by reference to the following detailed description when considered in connection with the accompanying drawings wherein:

FIG. 1 is a longitudinal cross sectional view of a needle assembly constructed in accordance with the present invention;

FIG. 1A is a cross sectional view taken substantially along lines 1A—1A of FIG. 1;

FIG. 2 is a longitudinal cross sectional view of a second embodiment of the present invention;

FIG. 3 is a longitudinal cross sectional view of a third embodiment of the present invention;

FIG. 3A is a cross sectional view taken substantially along lines 3A-3A of FIG. 3;

FIG. 4 is a longitudinal cross sectional view of a fourth embodiment of the present invention;

FIG. 5 is a longitudinal elevational view of a fifth embodiment of the present invention wherein a catheter is disposed adjacent to the hub portion of the assembly;

FIG. 6 is a longitudinal elevational view of the catheter being removed from the needle portion of the assembly;

FIG. 7 is a side elevational view of the catheter being completely removed from the needle of the assembly, the cap capping the distal tip of the needle;

FIG. 8 is a longitudinal elevational view of a sixth embodiment of the present invention, partially in cross section;

FIG. 9 is a longitudinal elevational view of the invention in friction fit over an IV port; and FIG. 10 is an longitudinal elevational view of the invention removed from the IV port, the cap of the invention capping the distal tip of the needle.

DETAILED DESCRIPTION OF THE INVENTION

A disposable needle assembly constructed in accordance with the present invention it is generally indicated at 10 in the Figures. The assembly 10 includes a combination of a hypodermic needle assembly generally shown at 12 and a catheter assembly generally shown at 14. The hypodermic needle assembly 12 includes a hub portion 16 having an inner cup shaped surface 18 adapted to be connected to a constricted portion 20 of a syringe barrel 22, as shown in FIG. 1. The hub portion 16 includes a passageway 24 extending therethrough. The hub portion 16 includes a radially outwardly extending flange 26 to secure the hub portion 16 to the syringe 22 with a luer-lock mechanism. Other locking mechanisms can be used to connect the hub portion 16 to the syringe 22.

A hollow metallic needle portion 28 includes a base portion 30 which is friction fit into the passageway 24. The hollow needle portion 28 is in fluid communication with the passageway 24. The hollow needle 28 includes a distal tip 32. The distal tip 32 is a sharp pointed beveled portion of the needle portion 28 adapted for puncturing the skin.

The assembly 10 includes a cap portion 34 having a neutral position, as shown in FIG. 1, along the needle portion 32 proximate to the hub 16 for exposing a length of the needle portion 28 and an extended position for capping the distal tip 32, as shown in FIG. 7. Cap 34 includes openings 35 to allow passage of needle portion 28. The cap portion 34 includes an inner surface 36 having a flange 38 extending therefrom and angling towards the hub portion 16. The cap 34 includes a closed corner 37 defined by the inner surface 36. In the extended position, the flange 38 deflects needle tip 32 into the closed corner 37 so that the needle tip 32 is prevented from reentering opening 35.

The catheter 14 includes a shaft portion 40 disposed about the exposed length of the needle portion 28 and exposing the distal tip 32. In this position, the distal tip can initiate a puncture through a patient's skin and into a vessel so that the shaft portion 40 of the catheter 14 can enter the patient's blood vessel.

The cap portion 34 includes an outer seating surface 42. The catheter 14 includes a hub portion 44 having an inner surface for releasably seating on the seating surface 42 whereby removal of the needle portion 28 from the shaft portion 40 moves the cap portion 34 to the extended position capping the distal tip 32 of the needle portion 28 as the hub 44 of the catheter 14 is unseated from the seating surface 42 of the cap portion 34. The invention thereby provides means for simultaneously capping the distal tip 32 of the needle portion 28 as the needle portion 28 is removed from the catheter 14.

A person administering the injection need not first remove the needle from the catheter and then independantly cap the end of the needle, but rather the needle is capped in the single motion of removing the needle from the catheter once the patient is catheterized. The invention thereby provides an efficient and effective means of preventing accidental puncture by a used needle during or after a catheterization process.

The seating surface 42 provides an outer frustoconical surface of the cap portion 34. The hub portion 44 of the catheter 14 includes an inner frustoconical surface 46 defining a seat in friction fit over the seating surface 42 of the cap portion 34 when the cap portion 34 is in the neutral position as shown in FIG. 1.

The hub portion 44 of the catheter 14 includes a radially outwardly extending annular flange 48. The flange 48 allows for a leur lock of the catheter, such as to another syringe.

The assembly 10 includes a tether generally indicated 50 for connecting the cap portion 34 to the hub 16 of the needle assembly 12 and limiting the extent that the cap portion 34 can be extended from the hub portion 16. By limiting the extent that the cap 34 can extend from the hub portion 12 to the length of the needle portion 28 in combination with the flange 38 deflects the needle tip 32 into the closed corner 37, the needle tip 32 is locked under the cap portion 34 when it is moved to the extended position. Thusly, flange 38 in combination with the tether 50 provides locking means for locking the cap portion 34 over the distal tip 32 of the needle portion 28 when the tether 50 is completely extended.

FIGS. 1–7 show five embodiments of the tether 50 constructed in accordance with the present invention.

Referring specifically to FIGS. 1 and IA, the tether 50 includes a substantially rigid and elongated tab member 52 having a first end portion 54 connected to the cap portion 34. The hub portion 16 includes a channel 56 extending therethrough, the tab member 52 being slideably disposed within and extending through the channel 56. An enlarged flanged end portion 58 of the tab member 52 limits the extent of movement of the tab member 52 through the channel 56 and the extent of movement of the cap portion 34 to the extended position. The channel 56 abuts against the flange 58 when the cap portion 34 is in the extended position thereby retaining at least a portion of the tab member 52 within the channel 56. Thusly, the channel 56 in combination with the flange portion 58 provide a stop means for limiting the extent of movement of the cap portion 34 and further combining with the flange 38 to lock the distal tip 32 of the needle portion 28 under the flange 38 when the cap portion 34 is moved to the extended position. The tab member 52 allows the user of the device to extend the cap potion 54 without coming in close proximity to the needle portion 28. This lowers the risk of contact between the user and the needle portion 28.

As shown in FIGS. 2–4, the tether 50' can be constructed in the form of a cord 60. In FIG. 2, the cord 60 includes a first end connected to the hub portion 16 and a second end connected to the cap member 34. In this embodiment, the cord 60 extends freely outside of the assembly 10.

FIGS. 3 and 4 show two constructions wherein the cord 60 is retained within the assembly.

Referring to FIGS. 3 and 3A, the cord 60 has a first end connected to the cap 34. The hub 16 includes a second passageway 68 extending therethrough. The cord 60 has a length thereof releasably contained within the passageway 68 when the cap 34 is in the neutral position and extending from the passageway 68 when the cap 34 is in the extended position. When the cap 34 is in the neutral position, the cord 60 does not extend freely outside of the assembly 10 but is rather neatly contained within the assembly.

The cord 60 includes means for limiting the amount of the cord 60 extending from the passageway 68. More specifically, the cord 60 has a second end connected to the hub 16. The length of the cord 60 thereby provides a means for limiting the extent to which the cap 34 can extend along the needle portion 28 away from the hub 16 to thereby cap the distal tip 32.

As shown in FIGS. 3 and 3A, the hub 16 includes a substantially arcuate member 70 connected thereto and spaced therefrom thereby defining the second passageway 68 therebetween. The hub 16 includes a plurality of projections 72 extending therefrom. The wall member 70 includes a plurality of projections 74 cooperating with the projections 72 of the hub 16 for connecting the wall member 70 to the hub 16. In this form, the wall 70 can be snapped onto the hub 16 during the assembling operation.

In FIG. 4, the cord 60 is contained within the assembly 10 by being wound around the portion of the needle portion 28 most proximate to the hub 16. The hub 16 includes an axially extending flange 76 which further contains the cap member 34 and cord 60 therein.

FIGS. 5-7 show another form of the tether means 50". The tether means 50" is in the form of an expandable sleeve 78 interconnecting the hub 16 and the cap 34 for perfecting a sealed closure about the entire length of the needle portion 28 when the cap 34 is in the extended position, as shown in FIG. 7. Specifically the sleeve 78 is pleated and includes a first end portion connected to the hub 16 and a second end portion connected to the cap 34.

The operation of the assembly is illustrated in FIGS. 5-7. In FIG. 5, the catheter 14 is seated over the cap 34, both being disposed adjacent to the hub 16. After catheterization of the patient, the syringe assembly 22 (not shown in FIGS. 5-7) having the hub portion 16 fixedly secured thereon is moved away from the catheter 14 withdrawing the needle portion 28 from the catheter 14 and extending the tether means 50" shown as the sheath 78. In any of the embodiments disclosed herein, the tether 50,50',50" means would be extended in a similar fashion. Once the cap 34 is extended so that the flange 38 is engaged by the distal tip 32 into the closed corner 37, the length of the tether means 50,50',50" limits the further extending of the cap 34 such that the flange 38 deflects the needle tip 32 from reentering cap opening 35 and into the closed corner 37 thereby irreversibly capping the needle. Upon further removal of the assembly 10 away from the catheter 14, the cap 34 becomes unseated from the second hub portion 44 of the catheter 14, as shown in FIG. 7. When done in a single motion, the withdrawal of the remainder of the assembly 10 from the catheter 14 extends and caps the cap member 34 over the distal tip 32 while simultaneously releasing the catheter 14 therefrom. Thusly, the present invention provides an effective and efficient means for catheterizing a patient and while simultaneously removing the needle and capping the needle of the assembly as the needle is withdrawn from the catheter.

Another embodiment of the present invention is shown in FIGS. 8-10. This embodiment of the present invention is adapted for intravenous tubing "piggy back" ports. Like numerals are again used to show similar structure between the several embodiments.

More specifically, the IV tubing has spliced therein a piggy back IV port 82. The IV port 82 includes a sealed end portion 84. The sealed end portion 84 includes diaphragm 86 in sealing engagement thereover.

Under normal conditions, fluid is fed from a tubing lead 88, or possibly a syringe (not shown) through a hypodermic needle which is inserted through the diaphragm 86 so that medicant or other fluids can be injected directly into the fluid carried by the IV catheter 80. This embodiment of the present invention provides flanges 90 extending axially from the end portion 92 of the cap member 44 for gripping the outer surface 94 of the IV port 84. The flanges 90 frictionally engage the outer surface 94 of the tubular port 82 thereby frictionally seating the cap member 34 thereon. The needle 28 defines a central axis extending through the cap 34, the flanges 90 being spaced about the needle 28.

The several embodiments of the present invention show that the present invention can be adapted in various manners to perform standard functions, the standard functions themselves causing the needle used therewith to be irreversibly capped.

The present invention further provides a novel method of catheterizing a patient. Generally, the method includes the steps of inserting a catheter assembly 10 into a patient's blood vessel and removing the needle 28 from the catheter tube 40 while simultaneously moving the cap 34 from the hub 16 of the needle 28 to a position capping the tip 32 of the needle 28. More specifically, the step of moving the cap 34 is further defined as retaining the cap 34 in the catheter hub 44 as the needle 28 is removed from the catheter 14 and releasing the cap 34 from the catheter 14 as the distal tip 32 of the needle 28 completely enters the cap 34. The cap 34 is released or unseated from the catheter 14 by limiting the length of displacement of the cap 34 from the hub 16 of the needle 28 to the length of the needle 28 by connecting the cap 34 to the hub 16 by the tethers 50,50',50".

The method of using this embodiment of the self-capping needle assembly includes the steps of inserting the needle 28 through the sealed end 84 of the catheter port 82 and seating the cap member 34 in engagement with the catheter port 84. The cap member 34 seated upon the catheter port 84 is shown in FIG. 9. The cap member 34 is disposed on the needle 28 adjacent the hub portion 16 of the needle 28. The needle 28 is removed from the catheter port 84 as shown in FIG. 10, while simultaneously moving the cap member 34 from the hub 16 of the needle 28 to the position capping the distal tip 32 of the needle 28.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A disposable needle assembly (10) comprising: a catheter assembly including a passageway therethrough; first hub means (16) defining proximal and distal ends thereof for connecting said needle assembly (10) to a fluid conduit, said first hub means (16) including a passageway (24) extending therethrough; a hollow needle portion (28) in fluid communication with said passageway (24) and including a distal tip (32) which is distal relative to said first hub means (16); cap means (34), including tether means (50,50',50") for connecting said cap means (34) to said first hub means (16) and limiting the extent that said cap means (34) can be extended from said first hub means (16), and locking means for locking said cap means (34) over said distal tip (32) when said tether means (50,50',50") is completely extended, said cap means having a neutral position along said needle portion (28) proximate to said first hub means (16) for exposing a length of said needle portion (28) and an extended position for capping said distal tip (32), said assembly characterized by said cap means (34) including releasable securing means for positively securing said cap means (34) with said catheter assembly as said needle portion (28) is disposed within said passageway of said catheter assembly and releasing said cap means (34) from said catheter assembly when said cap means are moved to said extended position whereby removal of said needle portion (28) from said passageway of the catheter assembly moves said cap means (34) relative to said needle portion to said extended position capping said distal tip (32) as said cap means (34) is unseated from said catheter assembly.

2. An assembly as set forth in claim 1 further characterized by said needle portion (28) defining a central axis extending through said cap means (34), said cap means (34) including a first axial end portion adjacent said first hub means (16) and an opposite second axial end, said releasable securing means including gripping means extending axially from said second end portion parallel to and spaced from said central axis for frictionally engaging an outer surface (94) of a tubular port (84) and frictionally seating the tubular port (84) therein.

3. An assembly as set forth in claim 2 further characterized by said gripping means includes a plurality of flanges (90) extending axially from said second end portion (92) for frictionally engaging the tubular port (84).

4. An assembly as set forth in claim 1 further characterized by said assembly (10) including a catheter (14) having a shaft portion (40) disposed about said exposed length of said needle portion (28) and exposing said distal tip (32) and second hub means (44) for releasably seating on said cap means (34) whereby removal of said needle portion (28) from said shaft portion (40) moves said cap means (34) relative to said needle portion (28) to said extended position capping said distal tip (32) as said second hub means (44) is unseated from said cap means (34).

5. An assembly as set forth in claim 4 further characterized by said cap means (34) including an outer frustoconical surface (42), said second hub means (44) including an inner frustoconical surface (46) in friction fit over said outer surface (42) of said cap means (34) when said cap means (34) is in said neutral position whereby moving of said second hub means (14) also moves said cap means (34) relative to said needle portion (28) to said extended position, when said friction fit being releasable when said cap means (34) is moved to said extended position.

6. An assembly as set forth in claim 5 further characterized by said second hub means (44) including an annular flange (48) extending radially outwardly from said outer surface thereof.

7. An assembly as set forth in claim 1 further characterized by said tether means (50) including a substantially rigid and elongated tab member (52) having a first end portion (54) connected to said cap means (34), said first hub means (16) including a channel (56) extending therethrough and said tab member (52) being slideably disposed within and extending through said channel (56), said tab member (52) including stop means (58) for limiting the extent of movement of said tab member (52) through said channel (56) and the extent of movement of said cap means (34) to said extended position; said channel (56) retaining at least a portion of said tab member (52) therein.

8. An assembly as set forth in claim 7 further characterized said stop means include a flanged second end portion (58) of said tab member (52).

9. An assembly as set forth in claim 1 further characterized by said tether means (50') including a cord (60) interconnecting said first hub means (16) and said cap means (66).

10. An assembly as set forth in claim 9 further characterized by said cord (60) having a first end connected to said cap means (34), said first hub means (16) including a second passageway (68) extending therethrough, said cord (60) having a length thereof releasably contained within said second passageway (68) when said cap means (34) is in said neutral position and extending from said second passageway (68) when said cap means (34) is in said extended position, said cord (60) including stop means for limiting the amount of said cord (60) extending from said passageway (68).

11. An assembly as set forth in claim 10 further characterized by said cord (60) having a second end connected to said first hub means (16).

12. An assembly as set forth in claim 11 further characterized by said first hub means (16) including a substantially arcuate wall member (70) connected thereto and spaced therefrom defining said second passageway (68) therebetween.

13. An assembly as set forth in claim 12 further characterized by said first hub means (16) including a plurality of projections (72) extending therefrom, said wall member (70) including a plurality of projections (74) for cooperating with said projections (72) on said first hub means (16) for connecting said wall member (70) to said first hub means (16).

14. An assembly as set forth in claim 9 further characterized by including an annular flange (76) extending axially from said first hub means (16) towards said cap means (34).

15. An assembly as set forth in claim 1 further characterized by said tether means (50") including expendable sleeve means (78) interconnecting said first hub means (16) and said cap means (34) for perfecting a sealed closure about the entire length of said needle portion (78) when said cap means (34) is in said extended position.

16. An assembly as set forth in claim 15 further characterized by said sleeve means (78) including a pleated sleeve (78) having a first end portion connected to said hub means (16) and a second end portion connected to said cap means (34).

17. An assembly as set forth in claim 1 further characterized by said cap means (34) including an inner cup shaped surface (36) opening towards said hub means (16), said locking means including at least one flange (38) extending into said cap means (34) from said inner surface (36) and angled towards said hub means (16) and a closed corner (37) opposite thereto within said cup-shaped inner surface (36), said tether means (50,50'50") biasing said cap means (34) towards said hub means (16) when said cap means (34) is in said extended position and said distal tip (32) being deflected into said closed corner (37) by said flange (38).

18. A method of catheterizing a patient, said method including the steps of: inserting at least a portion of a shaft (40) of catheter assembly (10) defining proximal and distal ends thereof into a patient's blood vessel, the catheter shaft (40) being disposed over a needle (28), and removing the needle (28) from the catheter shaft (40) while simultaneously moving a cap (34) from a hub (16) of the needle (28) to a position capping a distal tip (32) of the needle (28) which is distal relative to the hub (16) by friction fitting a hub (44) of the catheter (14) over the cap (34) and releasing friction fit when the cap (34) is moved to the position capping the distal tip (32) of the needle (28).

19. A method as set forth in claim 18 wherein said moving step is further defined as retaining the cap (34) seated within the catheter (14) as the needle (26) is removed from the catheter (14) and releasing the cap (34) from the catheter (14) as the distal tip (32) of the needle (28) completely enters the cap (34) and is locked therein.

20. A method as set forth in claim 18 wherein said releasing step is further defined by limiting the length of displacement of the cap (34) from the hub (16) of the needle (28) to the length of the needle (28) by connecting the cap (34) to the hub (16) with a tether (50,50',50").

21. A method of self-capping a needle, said method including the steps of: inserting a needle (28) defining a proximal and distal end thereof through a sealed end (84) of a catheter port (82); reversibly securing a cap member (34) with the catheter port (82), the cap member (34) being disposed on the needle (28) adjacent to a hub portion (16) of the needle (28) removing the needle (28) from the catheter port (84) while simultaneously moving the cap member (34) secured to the catheter port (82) from the hub (16) of the needle (28) to a position capping a distal tip (32) of the needle (28) which is distal relative to the hub (16); and releasing the cap member (34) from the catheter port (82).

22. A method as set forth in claim 21 wherein said seating step is further defined as gripping the catheter port (84) within a plurality of flanges extending from the axial distal end of the cap (34) to frictionally seat the flanges about the catheter port.

* * * * *